US00PP11848P2

(12) United States Plant Patent
Murray

(10) Patent No.: US PP11,848 P2
(45) Date of Patent: Apr. 24, 2001

(54) *METASEQUOIA GLYPTOSTROBOIDES* PLANT NAMED 'GOLDEN DAWN'

(76) Inventor: Kenneth W. Murray, 14 Cedar Ave., Roselle, Wilmington, DE (US) 19805

( * ) Notice: Subject to any disclaimer, the term of this patent is extended or adjusted under 35 U.S.C. 154(b) by 0 days.

(21) Appl. No.: 09/190,921

(22) Filed: Nov. 12, 1998

(51) Int. Cl.[7] ..... A01H 7/00
(52) U.S. Cl. ..... Plt./213
(58) Field of Search ..... Plt./213

(56) References Cited

U.S. PATENT DOCUMENTS

P.P. 9,346 * 10/1995 Shibata ..... Plt./213

* cited by examiner

*Primary Examiner*—Bruce R. Campell
*Assistant Examiner*—Wendy A. Baker
(74) *Attorney, Agent, or Firm*—Robert B. Famiglio, Esquire; Famiglio & Associates

(57) ABSTRACT

A new and distinct cultivar of *Metasequoia glyptostroboides* plant characterized by the globose shape, slow rate of growth, golden yellow color and stable dwarf characteristic.

2 Drawing Sheets

BACKGROUND

The present invention relates to a new and distinct cultivar of *Metasequoia glyptostroboides*, from the Taxodiaceae family, the novel characteristics of which reside particularly in the short, globose shape of the tree, slow rate of growth and golden yellow color.

The new cultivar, 'Golden Dawn', was discovered by Kenneth W. Murray and is the result of a seedling mutation from seeds of the species that were sown in 1986. The parentage of the seedling leading to 'Golden Dawn' is unknown. 'Golden Dawn' is the result of a seedling mutation that just happened to result in a yellow-leaved, slow growing plant. The mutation occurred naturally and was not induced. This plant was picked out of a large group of seedling because of its slow growth rate and golden yellow color of the leaves. It originated and was cultivated in Wilmington, Del. Thereafter, 'Golden Dawn' was successfully asexually reproduced in Kennedyville, Md. by Mr. Murray, by side grafting hardwood scions from 'Golden Dawn' onto an understock of an understock of an unknown cultivar of *Metasequoia glytostroboides*. Such asexual reproduction resulted in one hundred plants over a two year period, which have consistently displayed the short, bushy tree shape and dwarf characteristic after the first year of development. Propagations in 1997, included 25 plants in three gallon containers and 15 plants in the field. The propagations that were performed in 1998 included 60 plants which are in two gallon containers.

An interesting characteristic of the new cultivar, 'Golden Dawn', is its branching habit which is more dense than that of the species. The overall growth rate of 'Golden Dawn' is much slower than typical plants of the species. For example, the single straight trunk grows only 6" in height per year, distinguishing 'Golden Dawn' from known cultivars.

Other distinctive characteristics of the new cultivar are exemplified in the accompanying illustrations, taken during the summer of 1996 at the inventor's residence, wherein.

TECHNICAL DESCRIPTION

Figure 1:
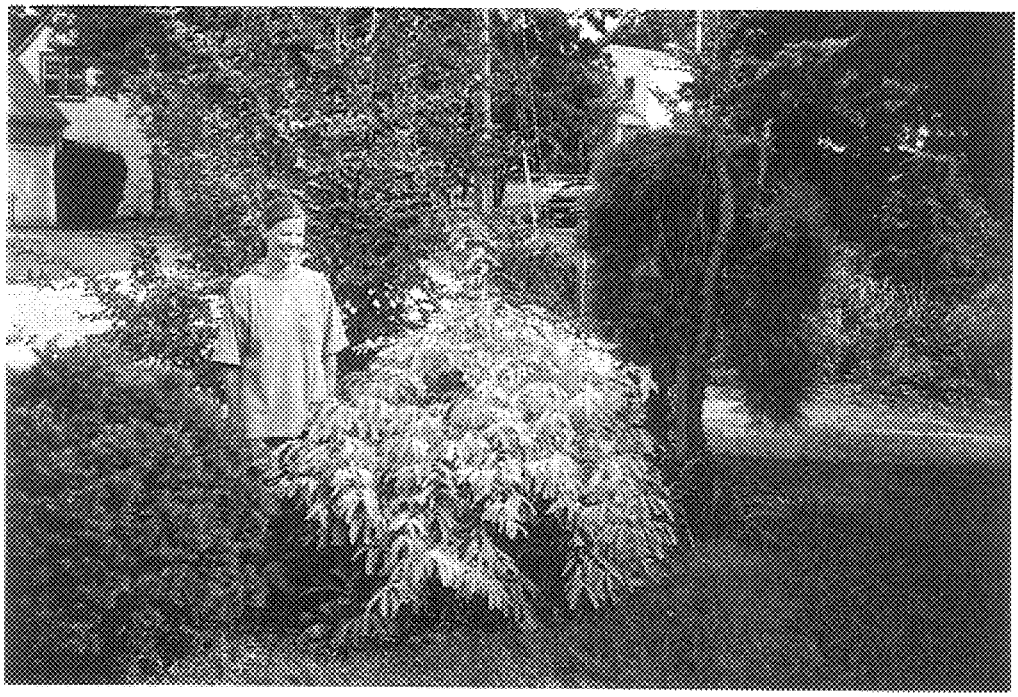
FIG. 1 is a photograph showing an adult tree of the new variety with a person standing next to the tree for size reference. The tree of the new variety in this figure is the one that resulted from the seed originally sown in 1986.
Figure 2:
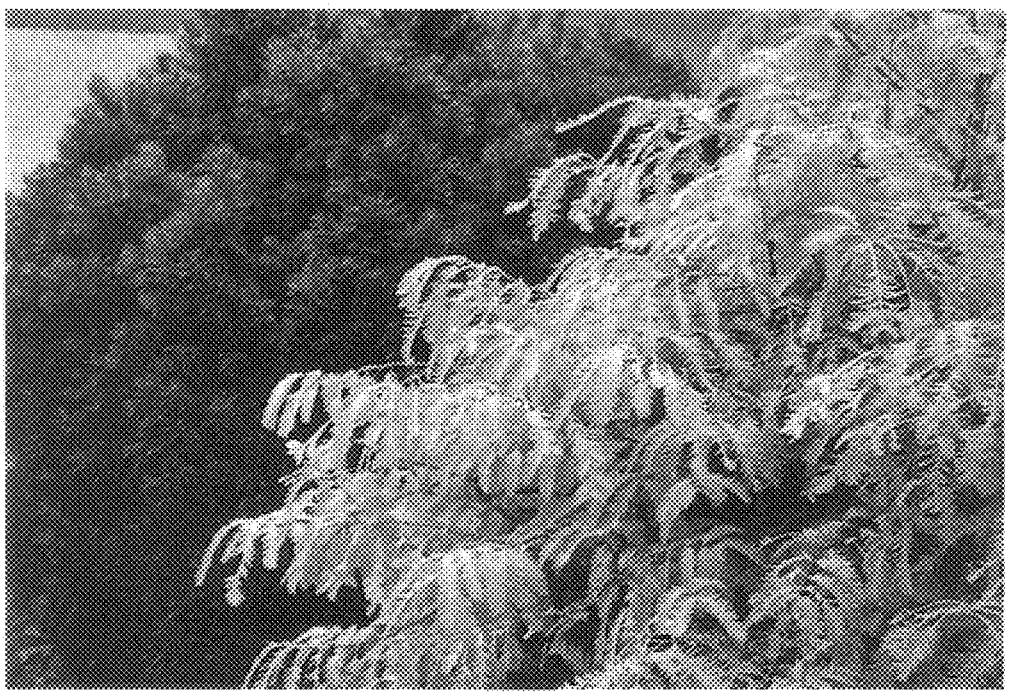
FIG. 2 is a close up photograph, showing the nature of the branches with adult leaves of a ten year old tree.
Figure 3:
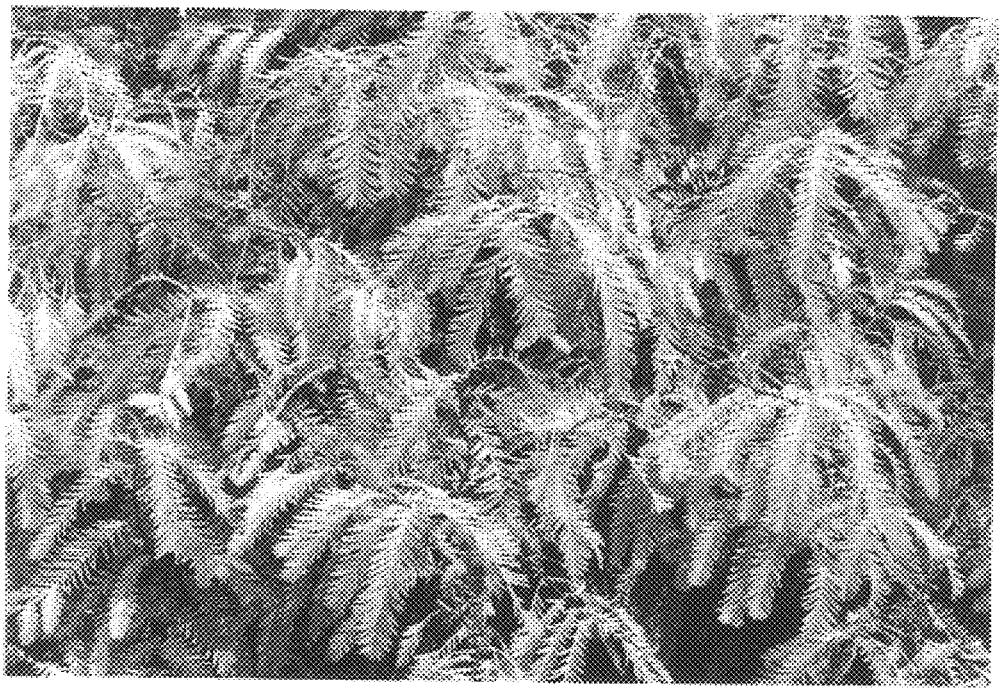
FIG. 3 is a close up of the leaves showing their golden color and opposite arrangement on the stem.
Figure 4:
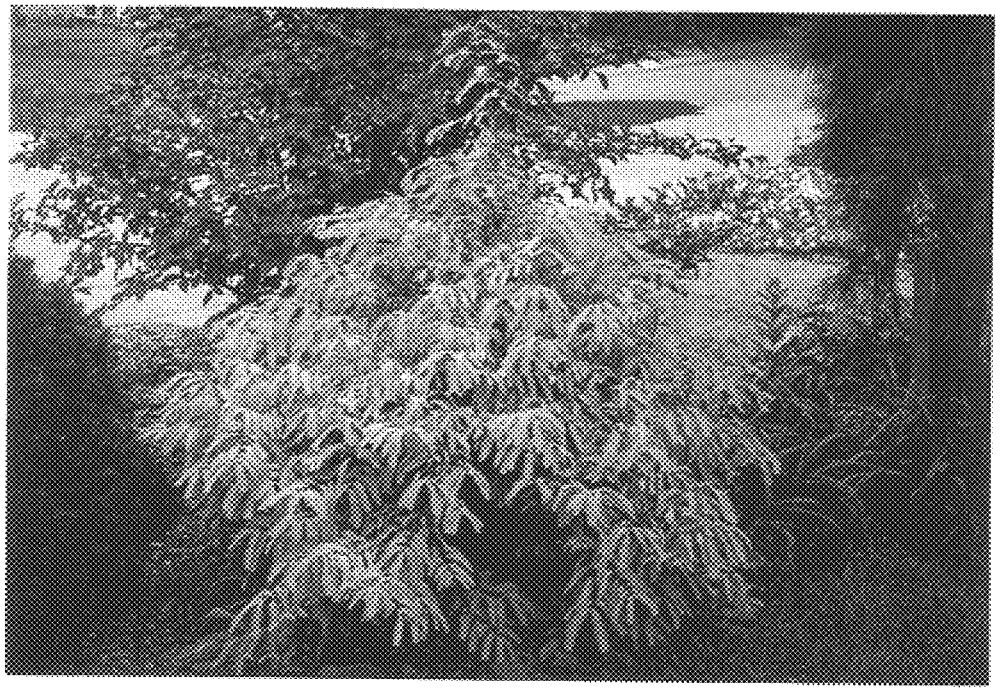
FIG. 4 shows the typical shape at the adult stage of development and depicts the golden yellow color, which is apparent in Spring, as accurately as is reasonably possible.

The following is a description in some detail of a ten year-old plant of the new cultivar of *Metasequoia glyptostroboides*, 'Golden Dawn', as grown in ambient outdoor conditions in Wilmington, Del.

Family: Taxodiaceae

Tree: Short, bushy globose, with a single straight trunk and branchlets of two kinds, persistent and deciduous. The persistent is bright reddish brown when young, shallowly ridged, carrying the deciduous branchlets, numerous vegetative buds and a few leaves. The green deciduous branchlets are up to about 3" long, usually opposite in arrangement, more or less horizontal, ribbed with long decurrent bases of up to 55–65 or more leaves.

Parentage: *Metasequoia glyptostroboides* (common type). The new cultivar, 'Golden Dawn', was reproduced by grafting hardwood scions of 'Golden Dawn' onto the understock of *Metasequoia glyptostroboides*. The mutation was not artificially induced, and the cause of the mutation is unknown. The precise parentage of the mutated seedling (from which the new cultivar was cultivated) is also unknown.

Foliage: Leaves are deciduous, opposite in arrangement, linear, flattened, straight or slightly curved, arranged comb-like, obtusely pointed, tapering abruptly towards the juncture with the branchlet. They are 5/16" and 1/16" broad on a ten-year-old tree. Buds are non-resinous (opposite), usually in pairs at the base of deciduous branchlets but sometimes solitary between the branchlets; ovid in shape, about 1/16" long and 1/32" wide, scales light reddish or yellowish brown with a linear keel, appearing stalked.

Location where the new cultivar was discovered and sexually reproduced: 'Golden Dawn' was first discovered in Wilmington, Del., and asexually reproduced, in Kennedyville, Md., by Kenneth W. Murray.

Color: The leaf color is predominantly golden yellow, (or Royal Horticultural Society Colour Chart #154-C). Due to variations in the intensity of sunlight, the color may vary up to 10-D. The brighter the sunlight, the lighter the color will be. Also, the older the leaves, the lighter their color will be due to their longer exposure to sunlight. In the Fall the leaves change to a warm brown color similar to R.H.S. 173-C. Both the upper and lower surfaces of the leaves display the same color characteristics. The bark is warm russet brown (R.H.S. 174-A), when young, becoming darker, grayish (R.H.S. 201-A), fissured, and then exfoliating in long, narrow strips with age. The branchlets are a red-brown (R.H.S. 173-A.

Reproductive

Organs: To date, there are no observable cones, or seeds.

Size: 5 feet in 10 years with a 4 foot spread.

Rate: Growth rate is slow, approximately 6 inches per year.

Culture: Transplants easily, performs best in moist, deep, well-drained, slightly acid soils, partial shade in afternoon. Seldom requires pruning due to small globose habit.

Hardiness: No known serious problems in Zone 7 and no anticipated problems in Zones 4 to 8, as evidenced in the typical species. However, 'Golden Dawn' has not been tested in Zones 4 to 8. There are no known problems relative to diseases and insects with 'Golden Dawn'.

The principal novel characteristics of the new cultivar, 'Golden Dawn,' as herein shown and described, are its globose shape, slow growth and golden yellow color. The unique combination of these distinctions and its ability to propagate make 'Golden Dawn' ideal for small landscapes.

I claim:

1. A new and distinct *Metasequoia glyptostroboides* plant, 'Golden Dawn', as described and illustrated.

* * * * *